(12) United States Patent
Hallek et al.

(10) Patent No.: US 6,562,351 B2
(45) Date of Patent: May 13, 2003

(54) PAPILLOMA TRUNCATED L1 PROTEIN AND FUSION PROTEIN CONSTRUCTS

(75) Inventors: Michael Hallek, Munich (DE); Alexander Burger, Munich (DE)

(73) Assignee: Medigene AG, Muenchen-Martinsried (DE)

(*) Notice: Subject to any disclaimer, the term of this patent is extended or adjusted under 35 U.S.C. 154(b) by 0 days.

(21) Appl. No.: 09/986,118

(22) Filed: Nov. 7, 2001

(65) Prior Publication Data

US 2003/0021806 A1 Jan. 30, 2003

Related U.S. Application Data

(62) Division of application No. 09/820,764, filed on Mar. 30, 2001, now Pat. No. 6,352,696, which is a continuation of application No. 09/026,896, filed on Feb. 20, 1998.

(51) Int. Cl.⁷ ............................................. A61K 39/12
(52) U.S. Cl. ................................ 424/204.1; 424/205.1; 424/184.1; 424/186.1; 435/6; 435/5; 530/300; 536/23.72
(58) Field of Search ...................... 424/204.1, 205.1, 424/184.1, 186.1; 435/69.1, 69.3, 5, 6; 530/300; 536/23.72

(56) References Cited

U.S. PATENT DOCUMENTS

| 5,618,536 | A | 4/1997 | Lowy et al. | 424/192.1 |
| 6,066,324 | A | 5/2000 | Gissmann et al. | 424/204.1 |
| 6,165,471 | A | 12/2000 | Garcea et al. | 424/186.1 |
| 6,228,368 | B1 * | 5/2001 | Gissmann et al. | 424/204.1 |

FOREIGN PATENT DOCUMENTS

| EP | 343 783 | 4/1989 |
| EP | 390 252 | 3/1990 |
| EP | A-0565794 | 10/1993 |
| WO | WO 93/20844 | 10/1933 |
| WO | WO 90/10459 | 9/1990 |
| WO | WO 93/00436 | 1/1993 |
| WO | WO 93/02184 | 2/1993 |
| WO | WO 93/21958 | 11/1993 |
| WO | WO 94/00152 | 1/1994 |
| WO | WO 94/05792 | 3/1994 |
| WO | WO 94/20137 | 9/1994 |
| WO | WO 94/23037 | 10/1994 |
| WO | WO 96/00583 | 1/1996 |
| WO | WO 96/11272 | 4/1996 |
| WO | WO 96/11274 | 4/1996 |
| WO | WO 96/19496 | 6/1996 |
| WO | WO 96/29091 | 9/1996 |
| WO | WO 98/04705 | 2/1998 |

OTHER PUBLICATIONS

Zhou et al., "Glycosylation of Human Papillomavirus Type 16 L1 Protein", *Virology*, 194, pp. 210–218, (1993).
Karasuyama, et al., "Establishment Of Mouse Lines Which Constitutively Secrete Large Quantities Of Interleukin 2, 3, 4 Or 5, Using Modified cDNA Expression Vectors", *Immunol.*, pp. 97–104, (1988).
G. Shaw et al., "Genetics", *A Conserved AU Sequence from the 3'Untranslated Region of GM–CSF mRNA Mediates Selective mRNA Degradation*, pp. 659–667 (1988).
M. Hagensee et al., "Journal of Virology", *Self–Assembly of Human Papillomavirus Type 1 Capsids by Expression of the L1 Protein Alone or by Coexpression of the L1 and L2 Capsid Proteins*, pp. 315–322 (1993).
XI et al., "Journal of General Virology", *Baculovirus expression of the human papillomavirus type 16 capsid proteins: detection of L1–L2 protein complexes*, pp. 2981–2988 (1991).
R.C. Rose et al., "Journal of Virology", vol. 67, No. 4, *Expression of Human Papillomavirus Type 11 L1Protein in Insect Cells: In Vivo and In Vitro Assembly of Viruslike Particles*, pp. 1936–1944, (Apr. 1993).
J. Zhou et al., "Virology", vol. 185, *Expression of Vaccinia Recombinant HPV 16 L1 and L2 ORF Proteins in Epithelial Cells is Sufficient for Assembly of HPV Virion–like Particles*, pp. 251–257, (1991).
M.S. Barbosa et al., "Journal of Virology", vol. 65 No. 1, *In Vitro Biological Activities of the E6 and E7 Genes Vary among Human Papillomaviruses of Different Oncogenic Potential*, pp. 292–298, (Jan. 1991).
J.M. Arbeit et al., "Journal of Virology", vol. 68, *Progressive Squamous Epithelial neoplasia in K14–Human Papillomavirus Type 16 Transgenic Mice*, pp. 4358–4368, (Jul. 1994).
P. Kaur et al., "J. Gen. Virology", vol. 70, *Immortalization of Primary Human Epithelial Cells by Cloned Cervical Carcinoma DNA Containing Human Papillomavirus Type 16 E6/E7 Open Reading Frames*, pp. 1261–1266, (1989).
L. Gao et al., "Journal of General Virology", vol. 75, *Immune Response to Human Papillomavirus Type 16 E6 Gene in a Live Vaccinia Vector*, pp. 157–164, (1994).
Tindle, et al., "Virology", Chimeric Hepatisi B Core Antigen Particles Containing B– and Th–Epitopes of Human Papillomavirus type 16 E7 Protein Induce Spec. Antibody and T–Helper . . . pp. 547–557 (1994).
Kirnbauer et al., "Proc. Natl. Acad. Science", Papillomavirus L1 major capsid protein self–assembles into *virus–like particles that are highly immunogenic*, vol. 89, pp. 12180–12184 (1992).
Carter et al., "Virology", *Expression of Human Papillomavirus Proteins in Yeast Saccharomyces Cerevisiae*, pp. 513–521 (1991).
Strike et al., Expression in *Escherichia coli* of Seven DNA Fragments Comprising the Complete L1 and L2 Open Reading Frames of Human Papillomavirus Type 6b and Localication of the 'Common Antigen' Region, Virology, pp. 543–555 (1989).

(List continued on next page.)

Primary Examiner—Ali R. Salimi
(74) Attorney, Agent, or Firm—Foley : Lardner

(57) ABSTRACT

Vaccine formulations comprising viral capsomeres are disclosed along with methods for their production. Therapeutic and prophylactic methods of use for the vaccine formulations are also disclosed.

16 Claims, No Drawings

OTHER PUBLICATIONS

Schafer et al., *Immune Response to Human Papillomavirus 16 L1E7 Chimeric Virus–Like Particles: Induction of Cytotoxic T Cells and Specific Tumor Protection*, "Int. J. Cancer" vol. 81, pp. 881–888 (1999).

Rose et al., *Expression of the full–length products of the human papillomavirus type 6b (HPB–6b) and HPV–11 L2 open reading frames by recombinant baculovirus, and antigenic comparisons with HPV–11 whole virus particles*. "Journal of General Virology", vol. 71, pp. 2725–2729 (1990).

Muller et al., *Chimeric papillomavirus–like Particles*, "Virology", pp. 93–111 (1997).

J. Zhou et al., "Virology", vol. 185, *Identification of the Nuclear Localization Signal of Human Papillomavirus Type 16 L1 Protein*, pp. 625–632, (1991).

R. Kirnbauer et al., "Journal of Virology", vol. 67 No. 12, *Efficient Self–Assembly of Human Papillomavirus Type 16 L1 and L1–L2 into Virus–Like Particles*, pp. 6929–6936, (Dec. 1993).

J.A. Rawls et al., "Journal of Virology", vol. 64 No. 12, *Chemical Synthesis of Human Papillomavirus Type 16 E7 Oncoprotein: Autonomous Protein Domains for Induction of Cellular DNA Synthesis and for trans Activation*, pp. 6121–6129, (Dec. 1990).

Paintsil, et al., "Virology", vol. 223, pp. 238–244, (1996).

Greenstone et al., "Proc. Natl. Acad. Sci. USA" *Chimeric Papillomavirus Virus–Like Particles Elicit Antitumor Immunity Against The E7 Oncoprotein in an HPV16 Tumor Model*, vol. 95, pp. 1800–1805, (Feb. 1998).

Zhou et al., "Abstract From the 13$^{th}$ International Papillomavirus Conference", *Determination of L1 Sequences Required for 1Assembly of Bovine Papillomavirus (BPV) Capsids*, Amsterdam, Netherlands, (Oct. 1994).

Altmann et al. "Towards HPV Vaccination," in *Viruses and Cancer*, Eds. Minson et al., Cambridge University Press, 71–80 (1994).

Balsley et al. "Progress in the Development of Human Papillomavirus Vaccines for HPV–11 and HPV–16/18 and Mapping of a Critical neutralizing Epitope" Abstract from HPV 2000 Int. Papillomavirus Conf. 366.

Breitburd et al. "Immunization With Viruslike Particles From Cottontail Rabbit Papillomavirus (CRPV) Can Protect Against Experimental CRPV Infection", *J. Virol.*, 69: 3959–3963 (1995).

Campo "Vaccination Against Papillomavirus in Cattle" in *Current Top Microbiol. Immunol: Human Pathogenic Papillomarivuses*, Ed. Zur Hausen, Springer Verlag, Berlin, 186:255–266 (1994).

Christensen et al. "Human Papillomavirus Types 6 and 11 Have Antigenically Distinct Strongly Immunogenic Conformationally Dependent Neutralizing Epitopes," *Virology*, 205: 329–335 (1994).

Christensen et al. "Assembled Baculovirus–Expressed Human Papillomavirus Type 11 L1 Capsid Protein Virus–Like Particles Are Recognized by Neutralizing Antibodies," *J. Gen. Virol.*, 75: 2271–2276 (1994).

Crum et al. "Coexpression of the Human Papillomvirus Type 16 E4 and L1 Open Reading Frames in Early Cervical Neoplasia" *Virology*, Academic Press, 178: 238–246 (1990).

Crum et al. "Human Papillomavirus Type 16 and Early Cervical Neoplasia" *N. Engl. J. Med.*, Boston, MA, 310: 880–883 (1984).

Dillner et al. "Antibodies Against Linear and Conformational Epitopes of Human Papillomavirus Type 16 that Independently Associate with Incident Cervical Cancer," *Int. J. Cancer*, 60: 377–382 (1995).

Doorbar et al. "Identification of the Human Papilloma Virus–1a E4 Gene Products" *EMBO J.*, 5: 355–362 (1986).

Fife et al. "A Dose–Ranging Study of the Safety and Immunogenicity Profiles of an HPV 11L1 VLP Candidate Vaccine in Young Healthy Woman" Abstract from HPV 2000 Int. Papillomavirus Conf. 364.

Ghim et al. "HPV–1 L1 Protein Expressed In cos Cells Displays Conformational Epitopes Found on Intact Virions", *Virology* 190: 548–552.

Gissmann "Human Papillomaviruses and Genital Cancer Seminars" in Cancer Biology, 3:253–261 (1992).

Greenfield et al. "Human Papillomavirus 16 E7 Protein is Associated with the Nuclear Matrix" *Proc. Natl. Acad. Sci. USA*, 88: 11217–11221 (1991).

Hagensee et al. "Three–Dimensional Structure of Vaccinia Virus–Produced Human Papillomavirus Type 1 Capsids," *J. Virol.*, 68:4503–4505 (1994).

Harry et al. "A Safety and Immunogenicity Trial of a Human Papillomavirus Type 16 L1 Virus–Like Particle Vaccine in Healthy Young Adult Human Volunteers" Abstract from HPV 2000 Int. Papillomavirus Conf. 362.

Heim et al. "Serum IgG, IgM, and IgA Reactivity to Human Papillomavirus Types 11 and 6 Virus–Like Particles in Different Gynecologic Patient Groups," *J. Infect. Dis.*, 172: 395–402 (1995).

Hofmann et al. "Sequence Determination of Human Papillomavirus Type 6a and Assembly of Virus–Like Particles in *Saccharomyces cerevisiae*," *Virology*, 209: 506–518 (1995).

Ikenberg "Human Papillomavirus DNA in Invasive Genital Carcinomas" in *Genital Papillomavirus Infections*, Eds. Gross et al., 87–112 (1990).

Jochmus et al. "Chimeric Virus–Like Particles of the Human Papillomavirus Type 16 (HPV 16) as a Prophylactic and Therapeutic Vaccine", *Archives of Medical Research*, 30: 269–274 (1999).

Jochmus–Kudielka et al. "Antibodies Against the Human Papillomavirus Type 16 Early Proteins in Human Sera: Correlation of Anti–E7 Reactivity with Cervical Cancer" J. Natl. Cancer Inst., 81: 1698–1704 (1989).

Kaufmann et al. "HPV16 L1E7 Chimeric Virus–Like Paticles Induce Specific HLA–Restricted T Cells In Human After In Vitro Vaccination", *Int. J. Cancer*, 92: 285–293 (2001).

Kirnbauer et al. "A Virus–Like Particle Enzyme–Linked Immunosorbent Assay Detects Serum Antibodies in a Majority of Women Infected With Human Papillomavirus Type 16," *J. Natl. Cancer Inst.*, 86: 494–499 (1994).

Le Cann et al. "Detection of Antibodies against Human Papillomavirus (HPV) Type 16 Virions by Enzyme–Linked Immunosorbent Assay Using Recombinant HPV 16 L1 Capsids Produced by Recombinant Baculovirus," *J. Clin. Microbiol.*, 33: 1380–1382 (1995).

Le Cann et al. "Self–Assembly of Human Papillomavirus Type 16 Capsids by Expression of the L1 Protein in Insect Cells," FEMS Microb. Lett., 117: 269–274 (1994).

Liu et al. "Mucosal Immunization with Papillomavirus Virus–Like Particles Elicits Systemic and Mucosal Immunity in Mice," *Virology*, 252: 39–45 (1998).

Lowy et al. "Genital Human papillomavirus Infection," *Proc. Nat. Acad. Sci. USA*, 91: 2436–2440 (1994).

Müller et al. "Papillomavirus Capsid Binding and Uptake by Cells from Different Tissues and Species," *J. Virol*, 69: 948–954 (1995).

Nasseri et al. "Genetic Analysis of CRPV Pathogenesis: the L1 Open Reading Frame is Dispensable for Cellular Transformation But Is Required for Papilloma Formation", *Virology*, Academic Press, 170: 321–325 (1989).

Nonnenmacher et al. "Serologic Response to Human Papillomavirus Type 16 (HPV–16) Virus–Like Particles in HPV–16 DNA–Positive Invasive Cervical Cancer and Cervical Intraepithelial Neoplasia Grade III Patients and Controls from Columbia and Spain," *J. Infect. Dis.*, 172: 19–24 (1995).

Parkin et al. "Estimates of the Worldwide Frequency of Sixteen Major Cancers in 1980", *Int. J. Cancer*, Alan R. Liss, Inc., 41: 184–197 (1988).

Poland et al. "A Randomized, Double–Blind, Placebo–Controlled Trial of the Immunogenicity and Reactogenicity of a Novel HPV 16 Vaccine: Preliminary Results" Abstract from HPV 2000 Int. Papillomavirus Conf. 363.

Pushko et al. "Sequence Variation in the Capsid Protein Genes of Human Papillomavirus Type 16" *J. Gen. Virol.*, 75: 911–916 (1994).

Roden et al. "Papillomavirus L1 Capsids Agglutinate Mouse Erythrocytes through a Proteinaceous Receptor," *J. Virol.*, 69: 5147–5151 (1995).

Roden et al. "In Vitro Generation and Type–Specific Neutralization of a Human Papillomavirus Type 16 Virion Pseudotype", *J. Virol.*, 70: 5875–5883 (1996).

Roden et al. "Interaction of Papillomaviruses with the Cell Surface," *J. Virol.*, 68: 7260–7266 (1994).

Rose et al. "Serological Differentiation of Human Papillomavirus Types 11, 16 and 18 Using Recombinant Virus–Like Particles," *J. Gen. Virol.*, 75: 2445–2449 (1994).

Rose et al. "Human Papillomavirus (HPV) Type 11 Recombinant Virus–Like Particles Induce the Formation of Neutralizing Antibodies and Detect HPV–Specific Antibodies in Human Sera," *J. Gen. Virol.*, 75: 2075–2079 (1994).

Rudolf et al. "Induction of HPV16 Capsid Protein–Specific Human T Cell Responses by Virus–Like Particles", *Biol. Chem.*, 380: 335–340 (1999).

Sapp et al. "Analysis of Type–Restricted and Cross–Reactive Epitopes on Virus–Like Paticles of Human Papillomavirus Type 33 and in Infected Tissues Using Monoclonal Antibodies to the Major Capsid Protein" J. Gen. Virology, 75: 3375–3383 (1994).

Sasagawa et al. "Synthesis and Assembly of Virus–Like Particles of Human Papillomaviruses Type 6 and Type 16 in Fission Yeast *Schizosaccharomyces pombe*," *Virology*, 206: 126–135 (1995).

Tindle et al. "Immune Response to Human Papillomaviruses and the Prospects for Human Papillovirus–Specific Immunization" in *Current Topics in Microbiol: Human Pathogenic Papillomaviruses*, Ed. zur Heusen, Springer Verlag, Berlin, 186:217–254 (1994).

Toes et al. "An Adenovirus Type 5 Region 1B–Encoded CTL Epitope–Mediating Tumor Eradication by CTL Clones Is Down–Modulated by an Activated ras Oncogene", *The Journal of Immunology*, 154: 3396–3405 (1995).

Toes et al. "Peptide Vaccination Can Lead to Enhanced Tumor Growth Through Specific T–cell Tolerance Induction", *Proc. Natl. Acad. Sci.*, 93: 7855–7860 (1996).

Volpers et al. "Binding and Internalization of Human Papillomavirus Type 33 Virus–Like Particles by Eukaryotic Cells," *J. Virol.*, 69: 3258–3264 (1995).

Volpers et al. "Assembly of the Major and the Minor Capsid Protein of Human Papillomavirus Type 33 into Virus–like and Tubular Structures in Insect Cells," *Virology*, Academic Press, 200: 504–512 (1994).

Von Knebel Doeberitz et al. "Correlation of Modified Human Papillomavirus Early Gene Expression with Altered Growth Properties in C4–1 Cervical Carcinoma Cells" *Cancer Res.*, 48: 3780–3786 (1988).

Wettstein "State of Viral DNA and Gene Expression in Benign vs. Malignant Tumors" in *Papillomaviruses and Human Cancer*, Eds. H. Pfister, CRC Press, Boca Raton, Florida, USA, 155–179 (1990).

Wikstrom et al. "Identification of Human Papillomavirus Seroconversions," *J. Gen. Virol.*, 76: 529–539 (1995).

Zhou et al. "Synthesis and Assembly of Infectious Bovine Papillomavirus Particles in Vitro" *J. Gen. Virol.*, Great Britain, 74: 763–768 (1993).

Zur Hausen "Papillomaviruses as Carcinomaviruses" in *Advances in Viral Oncology*, Eds. Klein et al., Raven Press, New York 8:1–26 (1989).

* cited by examiner

PAPILLOMA TRUNCATED L1 PROTEIN AND FUSION PROTEIN CONSTRUCTS

This application is a divisional of U.S. application Ser. No. 09/820,764, filed Mar. 30, 2001, now U.S. Pat. No. 6,352,696, which is a continuation of U.S. application Ser. No. 09/026,896, filed Feb. 20, 1998.

FIELD OF THE INVENTION

The present invention relates to vaccine formulations comprising papilloma virus proteins, either as fusion proteins, truncated proteins, or truncated fusion proteins. The invention further embraces methods for producing capsomeres of the formulations, as well as prophylactic and therapeutic methods for their use.

BACKGROUND

Infections with certain high-risk strains of genital papilloma viruses in humans (HPV)—for example, HPV 16, 18, or 45—are believed to be the main risk factor for the formation of malignant tumors of the anogenital tract. Of the possible malignancies, cervical carcinoma is by far the most frequent: according to an estimate by the World Health Organization (WHO), almost 500,000 new cases of the disease occur annually. Because of the frequency with which this pathology occurs, the connection between HPV infection and cervical carcinoma has been extensively examined, leading to numerous generalizations.

For example, precursor lesions of cervical intraepithelial neoplasia (CIN) are known to be caused by papilloma virus infections [Crum, New Eng. J. Med. 310:880–883 (1984)]. DNA from the genomes of certain HPV types, including for example, strains 16, 18, 33, 35, and 45, have been detected in more than 95% of tumor biopsies from patients with this disorder, as well as in primary cell lines cultured from the tumors. Approximately 50 to 70% of the biopsied CIN tumor cells have been found to include DNA derived only from HPV 16.

The protein products of the HPV 16 and HPV 18 early genes E6 and E7 have been detected in cervical carcinoma cell lines as well as in human keratinocytes transformed in vitro [Wettstein, et al., in PAPILLOMA VIRUSES AND HUMAN CANCER, Pfister (Ed.), CRC Press: Boca Raton, Fla. 1990 pp 155–179] and a significant percentage of patients with cervical carcinoma have anti-E6 or anti-E7 antibodies. The E6 and E7 proteins have been shown to participate in induction of cellular DNA synthesis in human cells, transformation of human keratinocytes and other cell types, and tumor formation in transgenic mice [Arbelt, et al., J. Virol., 68:4358–4364 (1994); Auewarakul, et al., Mol. Cell. Biol. 14:8250–8258 (1994); Barbosa. et al., J. Virol. 65:292–298 (1991); Kaur, et al, J. Gen. Virol. 70:1261–1266 (1989); Schlegel, et al., EMBO J., 7:3181–3187 (1988)]. The constitutive expression of the E6/E7 proteins appears to be necessary to maintain the transformed condition of HPV-positive tumors.

Despite the capacity of some HPV strains to induce neoplastic phenotypes in vivo and in vitro, still other HPV types cause benign genital warts such as condylomata acuminata and are only rarely associated with malignant tumors [Ikenberg, In Gross, et al., (eds.) GENITAL PAPILLOMAVIRUS INFECTIONS, Springer Verlag: Berlin, pp., 87–112]. Low risk strains of this type include, for example, HPV 6 and 11.

Most often, genital papilloma viruses are transmitted between humans during intercourse which in many instances leads to persistent infection in the anogenital mucous membrane. While this observation suggests that either the primary infection induces an inadequate immune response or that the virus has developed the ability to avoid immune surveillance, other observations suggest that the immune system is active during primary manifestation as well as during malignant progression of papilloma virus infections [Altmann et al. in VIRUSES AND CANCER, Minson et al., (eds.) Cambridge University Press, (1994) pp. 71–80].

For example, the clinical manifestation of primary infection by rabbit and bovine papilloma virus can be prevented by vaccination with wart extracts or viral structural proteins [Altmann, et al., supra; Campo, Curr. Top. In Microbiol and Immunol. 186:255–266 (1994); Yindle and Frazer, Curr. Top. In Microbiol. and Immunol. 186;217–253 (1994)]. Rodents previously vaccinated with vaccinia recombinants encoding HPV 16 early proteins E6 or E7, or with synthetic E6 or B7 peptides, are similarly protected from tumor formation after inoculation of HPV 16 transformed autologous cells [Altman, et al., supra; Campo, et al., supra; Yindle and Frazer, et al. supra]. Regression of warts can be induced by the transfer of lymphocytes from regressor animals following infection by animal papilloma viruses. Finally, in immunosuppressed patients, such as, for example, recipients of organ transplants or individuals infected with HIV, the incidence of genital warts. CIN, and anogenital cancer is elevated.

To date, no HPV vaccinations have been described which comprise human papilloma virus late L1 protein in the form of capsomeres which are suitable both for prophylactic and therapeutic purposes. Since the L1 protein is not present in malignant genital lesions, vaccination with L1 protein does not have any therapeutic potential for these patients. Construction of chimeric proteins, comprising amino acid residues from L1 protein and, for example E6 or E7 protein, which give rise to chimeric capsomeres, combines prophylactic and therapeutic functions of a vaccine. A method for high level production of chimeric capsomeres would therefore be particularly desirable, in view of the possible advantages offered by such a vaccine for prophylactic and therapeutic intervention.

Thus there exists a need in the art to provide vaccine formulations which can prevent or treat HPV infection. Methods to produce vaccine formulations which overcome problems known in the art to be associated with recombinant HPV protein expression and purification would manifestly be useful to treat the population of individuals already infected with HPV as well as useful to immunize the population of individuals susceptible to HPV infection.

SUMMARY OF THE INVENTION

The present invention provides therapeutic and prophylactic vaccine formulations comprising chimeric human papilloma capsomeres. The invention also provides therapeutic methods for treating patients infected with an HPV as well as prophylactic methods for preventing HPV infection in a susceptible individual. Methods for production and purification of capsomeres and proteins of the invention are also contemplated.

In one aspect of the invention, prophylactic vaccinations for prevention of HPV infection are considered which incorporate the structural proteins L1 and L2 of the papilloma virus. Development of a vaccine of this type faces significant obstacles because papilloma viruses cannot be propagated to adequate titers in cell cultures or other experimental systems to provide the viral proteins in sufficient quantity for economical vaccine production. Moreover, recombinant methodologies to express the proteins are not always straightforward and often results in low protein yield. Recently, virus-like particles (VLPs), similar in make up to viral capsid structures, have been described which are formed in Sf-9 insect cells upon expression of the viral proteins L1 and L2 (or L1 on its own) using recombinant vaccinia or baculovirus. Purification of the VLPs can be achieved very simply by means of centrifugation in CsCl or sucrose gradients [Kimbauer, et al., *Proc. Natl. Acad. Sci.* (USA), 99:12180–12814 (1992): Kirnbaurer, et al., *J. Virol.* 67:6929–6936 (1994); Proso, et al., *J. Virol.* 6714:1936–1944 (1992): Sasagawa, et al., *Virology* 2016:126–195 (1995): Volpers, et al., *J. Virol.* 69:3258–3264 (1995); Zhou, et al., *J. Gen. Virol.* 74:762–769 (1993): Zhou, et al., *Virology* 185:251–257 (1991)]. WO 93/02184 describes a method in which papilloma virus-like particles (VLPs) are used for diagnostic applications or as a vaccine against infections caused by the papilloma virus. WO 94/00152 describes recombinant production of L1 protein which mimics the conformational neutralizing epitope on human and animal papilloma virions.

In another aspect of the invention, therapeutic vaccinations are provided to relieve complications of, for example, cervical carcinoma or precursor lesions resulting from papilloma virus infection, and thus represent an alternative to prophylactic intervention. Vaccinations of this type may comprise early papilloma virus proteins, principally E6 or E7, which are expressed in the persistently infected cells. It is assumed that, following administration of a vaccination of this type, cytotoxic T-cells might be activated against persistently infected cells in genital lesions. The target population for therapeutic intervention is patients with HPV-associated pre-malignant or malignant genital lesions. PCT patent application WO 93/20844 discloses that the early protein E7 and antigenic fragments thereof of the papilloma virus from HPV or BPV is therapeutically effective in the regression, but not in the prevention, of papilloma virus tumors in mammals. While early HPV proteins have been produced by recombinant expression in *E. coli* or suitable eukaryotic cell types, purification of the recombinant proteins has proven difficult due to inherent low solubility and complex purification procedures which generally require a combination of steps, including ion exchange chromatography, gel filtration and affinity chromatography.

According to the present invention, vaccine formulations comprising papilloma virus capsomeres are provided which comprise either: (i) a first protein that is an intact viral protein expressed as a fusion protein comprised in part of amino acid residues from a second protein; (ii) a truncated viral protein: (iii) a truncated viral protein expressed as a fusion protein comprised in part of amino acid residues from a second protein, or (iv) some combination of the three types of proteins. According to the invention, vaccine formulations are provided comprising capsomeres of bovine papilloma virus (BPV) and human papilloma virus. Preferred bovine virus capsomeres comprise protein from bovine papilloma virus type I. Preferred human virus capsomeres comprise proteins from any one of human papilloma virus strains HPV6, HPV11, HPV16, HPV18, HPV33, HPV35, and HPV45. The most preferred vaccine formulations comprise capsomeres comprising proteins from HPV16.

In one aspect, capsomere vaccine formulations of the invention comprise a first intact viral protein expressed as a fusion protein with additional amino acid residues from a second protein. Preferred intact viral proteins are the structural papilloma vial proteins L1 and L2. Capsomeres comprised of intact viral protein fusions may be produced using the L1 and L2 proteins together or the L1 protein alone. Preferred capsomeres are made up entirely of L1 fusion proteins, the amino acid sequence of which is set out in SEQ ID NO: 2 and encoded by the polynucleotide sequence of SEQ ID NO: 1. Amino acids of the second protein can be derived from numerous sources (including amino acid residues from the first protein) as long as the addition of the second protein amino acid residues to the first protein permits formation of capsomeres. Preferably, addition of the second protein amino acid residues inhibits the ability of the intact viral protein to form virus-like particle structures; most preferably, the second protein amino acid residues promote capsomere formation. In one embodiment of the invention, the second protein may be any human tumor antigen, viral antigen, or bacterial antigen which is important in stimulating an immune response in neoplastic or infectious disease states. In a preferred embodiment, the second protein is also a papilloma virus protein. It also preferred that the second protein be the expression product of papilloma virus early gene. It is also preferred, however, that the second protein be selected from group of E1, E2, E3, E4, E5, E6, and E7—early gene products encoded in the genome of papilloma virus strains HVP6, HPV11, HPV18, HPV33, HPV35, or HPV 45. It is most preferred that the second protein be encoded by the HPV16 E7 gene, the open reading frame of which is set out in SEQ ED NO: 3. Capsomeres assembled from fusion protein subunits are referred to herein as chimeric capsomeres. In one embodiment, the vaccine formulation of the invention is comprised of chimeric capsomeres wherein L1 protein amino acid residues make up approximately 50 to 99% of the total fusion protein amino acid residues. In another embodiment, L1 amino acid residues make up approximately 60 to 90% of the total fusion protein amino acid residues; in a particularly preferred embodiment, L1 amino acids comprise approximately 80% of the fusion protein amino acid residues.

In another aspect of the invention, capsomere vaccine formulations are provided that are comprised of truncated viral proteins having a deletion of one or more amino acid residues necessary for formation of a virus-like particle. It is preferred that the amino acid deletion not inhibit formation of capsomeres by the truncated protein, and it is most preferred that the deletion favor capsomere formation. Preferred vaccine formulations of this type include capsomeres comprised of truncated L1 with or without L2 viral proteins. Particularly preferred capsomeres are comprised of truncated L1 proteins. Truncated proteins contemplated by the invention include those having one or more amino acid residues deleted from the carboxy terminus of the protein, or one or more amino acid residues deleted from the amino terminus of the protein, or one or more amino acid residues deleted from an internal region (i.e., not from either terminus) of the protein. Preferred capsomere vaccine formulations are comprised of proteins truncated at the carboxy terminus. In formulations including L1 protein derived from HPV16, it is preferred that from 1 to 34 carboxy terminal amino acid residues are deleted. Relatively shorter deletions are also contemplated which offer the advantage of minor modification of the antigenic properties of the L1 proteins and the capsomeres formed thereof. It is most preferred, however, that 34 amino acid residues be deleted from the L1 sequence, corresponding to amino acids 472 to 505 in HPV16 set out in SEQ ID NO: 2, and encoded by the polynucleotide sequence corresponding to nucleotides 1414 to 1516 in the human HPV16 L1 coding sequence set out in SEQ ID NO: 1.

When a capsomere vaccine formulation is made up of proteins bearing an internal deletion, it is preferred that the deleted amino acid sequence comprise the nuclear localization region of the protein. In the L1 protein of HPV 16, the nuclear localization signal is found from about amino acid residue 499 to about amino acid residue 505. Following expression of L1 proteins wherein the NLS has been deleted, assembly of capsomere structures occurs in the cytoplasm of the host cell. Consequently, purification of the capsomeres is possible from the cytoplasm instead of from the nucleus where intact L1 proteins assemble into capsomeres. Capsomeres which result from assembly of truncated proteins wherein additional amino acid sequences do not replace the deleted protein sequences are necessarily not chimeric in nature.

In still another aspect of the invention, capsomere vaccine formulations are provided comprising truncated viral protein expressed as a fusion protein adjacent amino acid residues from a second protein. Preferred truncated viral proteins of the invention are the structural papilloma viral proteins L1 and L2. Capsomeres comprised of truncated viral protein fusions may he produced using L1 and L2 protein components together or L1 protein alone. Preferred capsomeres are those comprised of L1 protein amino acid residues. Truncated viral protein components of the fusion proteins include those having one or more amino acid residues deleted from the carboxy terminus of the protein, or one or more amino acid residues deleted from the amino terminus of the protein, or one or more amino acid residues deleted from an internal region (i.e., not from either terminus) of the protein. Preferred capsomere vaccine formulations are comprised of proteins truncated at the carboxy terminus. In those formulations including L1 protein derived from HPV16, it is preferred that from 1 to 34 carboxy terminal amino acid residues are deleted. Relatively shorter deletions are also contemplated that offer the advantage of minor modification of the antigenic properties of the L1 protein component of the fusion protein and the capsomeres formed thereof. It is most preferred, however, that 34 amino acid residues be deleted from the L1 sequence, corresponding to amino acids 472 to 505 in HPV16 set out in SEQ ID NO: 2, and encoded by the polynucleotide sequence corresponding to nucleotides 1414 to 1516 in the human HPV16 L1 coding sequence set out in SEQ ID NO: 1. When the vaccine formulation is comprised of capsomeres made up of proteins bearing an internal deletion, it is preferred that the deleted amino acid sequence comprise the nuclear localization region, or sequence, of the protein.

Amino acids of the second protein can be derived from numerous sources as long as the addition of the second protein amino acid residues to the first protein permits formation of capsomeres. Preferably, addition of the second protein amino acid residues promotes or favors capsomere formation. Amino acid residues of the second protein can be derived from numerous sources, including amino acid residues from the first protein. In a preferred embodiment, the second protein is also a papilloma virus protein. It also preferred that the second protein be the expression product of papilloma virus early gene. It is most preferred, however, that the second protein be selected from group of early gene products encoding by papilloma virus E1, E2, B, E4, E5, E6, and E7 genes. In one embodiment, the vaccine formulation of the invention is comprised of chimeric capsomeres wherein L1 protein amino acid residues make up approximately 50 to 99% of the total fusion protein amino acid residues. In another embodiment, L1 amino acid residues make up approximately 60 to 90% of the total fusion protein amino acid residues; in a particularly preferred embodiment, L1 amino acids comprise approximately 80% of the fission protein amino acid residues.

In a preferred embodiment of the invention, proteins of the vaccine formulations are produced by recombinant methodologies, but in formulations comprising intact viral protein, the proteins may be isolated from natural sources. Intact proteins isolated from natural sources may be modified in vitro to include additional amino acid residues to provide a fusion protein of the invention using covalent modification techniques well known and routinely practiced in the art. Similarly, in formulations comprising truncated viral proteins the proteins may be isolated from natural sources as intact proteins and hydrolyzed in vitro using chemical hydrolysis or enzymatic digestion with any of a number of site-specific or general proteases, the truncated protein subsequently modified to include additional amino acid resides as described above to provide a truncated fusion protein of the invention.

In producing capsomeres, recombinant molecular biology techniques can be utilized to produce DNA encoding either the desired intact protein, the truncated protein, or the truncated fusion protein. Recombinant methodologies required to produce a DNA encoding a desired protein are well known and routinely practiced in the art. Laboratory manuals, for example Sambrook, et al., (eds.), MOLECULAR CLONING: A LABORATORY MANUAL. Cold Spring Harbor Press: Cold Spring Harbor, N.Y. (1989) and Ausebel et al., (eds.). PROTOCOLS IN MOLECULAR BIOLOGY, John Wiley & Sons. Inc. (1994–1997), describe in detail techniques necessary to carry out the required DNA manipulations. For large-scale production of chimeric capsomeres, protein expression can be carried out using either viral or eukaryotic vectors. Preferable vectors include any of the well known prokaryotic expression vectors, recombinant baculoviruses, COS cell specific vectors, vaccinia recombinants, or yeast-specific expression constructs. When recombinant proteins are used to provide capsomeres of the invention, the proteins may first be isolated from the host cell of its expression and thereafter incubated under conditions which permit self-assembly to provide capsomeres. Alternatively, the proteins may be expressed under conditions wherein capsomeres are formed in the host cell.

The invention also contemplates processes for producing capsomeres of the vaccine formulations. In one method, L1 proteins are expressed from DNA encoding six additional histidines at the carboxy terminus of the L1 protein coding sequence L1 proteins expressed with additional histidines (His L1 proteins) are most preferably expressed in E. coli and the His L1 proteins can be purified using nickel affinity chromatography. His L1 proteins in cell lysate are suspended in a denaturation buffer, for example, 6 M guanidine hydrochloride or a buffer of equivalent denaturing capacity, and then subjected to nickel chromatography. Protein eluted from the nickel chromatography step is renatured, for example in 150 mM NaCl, 1 mM $CaCl_2$, 0.01% Triton-X 100, 10 mM HEPES (N-2-hydroxymethyl piperazine-N'-2 ethane sulfonic acid), pH 7.4. According to a preferred method of the invention, assembly of capsomeres takes place after dialysis of the purified proteins, preferably after dialysis against 150 mM NaCl, 25 mM $Ca^{2+}$, 10% DMSO (dimethyl sulfoxide). 0.1% Triton-X 100. 10 mM Tris [tris-(hydroxymethyl) amino-methane] acetic acid with a pH value of 5.0.

Formation of capsomeres can be monitored by electron microscopy, and, in instances wherein capsomeres are comprised of fusion proteins, the presence of various protein components in the assembled capsomere can be confirmed by Western blot analysis using specific antisera.

According to the present invention, methods are provided for therapeutic treatment of individuals infected with HPV comprising the step of administering to a patient in need thereof an amount of a vaccine formulation of the invention effective to reduce the level of HPV infection. The invention also provide methods for prophylactic treatment of individuals susceptible to HPV infection comprising the step of administering to an individual susceptible to HPV infection an amount of a vaccine formulation of the invention effective to prevent HPV infection. While infected individuals can be easily identified using standard diagnostic techniques, susceptible individuals may be identified, for example, as those engaged in sexual relations with an infected individual. However, due to the high frequency of HPV infection, all sexually active persons are susceptible to papilloma virus infection.

Administration of a vaccine formulation can include one or more additional components such as pharmaceutically acceptable carriers, diluents, adjuvants, and/or buffers. Vaccines may be administered at a single time or at multiple times. Vaccine formulation of the invention may be delivered by various routes including, for example, oral, intravenous, intramuscular, nasal, rectal, transdermal, vaginal, subcutaneous, and intraperitoneal administration.

Vaccine formulations of the invention offer numerous advantages when compared to conventional vaccine preparations. As part of a therapeutic vaccination, capsomeres can promote elimination of persistently infected cells in, for example, patients with CIN or cervical carcinoma. Additionally, therapeutic vaccinations of this type can also serve a prophylactic purpose in protecting patients with CIN lesions from re-infection. As an additional advantage, capsomeres can escape neutralization by pre-existing anticapsid antibodies and thereby posses longer circulating half-life as compared to chimeric virus-like particles.

Vaccine formulations comprising chimeric capsomeres can provide the additional advantage of increased antigenicity of both protein components of the fusion protein from which the capsomere is formed. For example, in a VLP, protein components of the underlying capsomere may be buried in the overall structure as a result of internalized positioning within the VLP itself. Similarly, epitopes of the protein components may be sterically obstructed as, a result of capsomere-to-capsomere contact, and therefore unaccessible for eliciting an immune response. Preliminary results using L1/E7 fusion proteins to produce VLPs support this position in that no antibody response was detected against the E7 component. This observation is consistent with previous results which indicate that the carboxy terminal region of L1 forms inter-pentameric arm structures that allow assembly of capsomeres into capsids [Garcia, et al.,*J. Virol.* 71: 2988–2995 (1997)]. Presumably in a chimeric capsomere structure, both protein components of the fusion protein substructure are accessible to evoke an immune response. Capsomere vaccines would therefore offer the additional advantage of increased antigenicity against any protein component, including, for example, neutralizing epitopes from other virus proteins, expressed as a fusion with L1 amino acid sequences.

DETAILED DESCRIPTION OF THE INVENTION

The present invention is illustrated by the following examples. Example 1 describes construction of expression vectors to produce fusion, or chimeric, viral proteins. Example 2 relates to generation of recombinant baculoviruses for expression of viral proteins. Example 3 addresses purification of capsomeres. Example 4 describes an immunization protocol for production of antisera and monoclonal antibodies. Example 5 provides a peptide ELISA to quantitate capsomere formation. Example 6 describes an antigen capture ELISA to quantitate capsomere formation. Example 7 provides a hemagglutinin assay to assay for the induction of neutralizing antibodies.

EXAMPLE 1

Construction of Chimeric L1 Genes

DNA, encoding the BPV 16 L1 open reading frame was excised from plasmid 16–114/k-L1/L2-pSynxtVI⁻ [Kirnbauer et al.,*J. Virol.* 67:6929–6936 (1994)] using BglII and the resulting fragment subcloned into pUC19 (New England Biolabs, Beverly, Mass.) previously linearized at the unique BamHI restriction site. Two basic expression constructs were first generated to permit subsequent insertion of DNA to allow fusion protein expression. One construct encoded HPV 16 L1Δ310 having a nine amino acid deletion: the deleted region was known to show low level homology with all other papilloma virus L1 proteins. The second construct, HPV 16 L1 ΔC, encoded a protein having a 34 amino acid deletion of the carboxy terminal L1 residues. Other constructs include an EcoRV restriction site at the position of the deletion for facilitated insertion of DNA encoding other protein sequences. Addition of the EcoRV site encodes two non-L1 protein amino acids, aspartate and isoleucine.

A. Generation of an HPV 16 L1Δ310 Expression Construct

Two primers (SEQ ID NOs: 5 and 6) were designed to amplify the pUC19 vector and the complete HPV 16 L1 coding sequence, except nucleotides 916 through 942 in SEQ ID NO: 1. Primers were synthesized to also introduce a unique EcoRV restriction site (underlined in SEQ ID NOs: 5 and 6) at the termini of the amplification product.

CCCC<u>GATATC</u>GCCTTTAATGTATAAATCGTCTGG    SEQ ID NO:5

CCCC<u>GATATC</u>TCAAATTATTTTCCTACACCTAGTG    SEQ ID NO:6

The resulting PCR product was digested with EcoRV to provide complementary ends and the digestion product circularized by ligation. Ligated DNA was transformed into *E. coli* using standard techniques and plasmids from resulting colonies were screened for the presence of an EcoRV restriction site. One clone designated HPV 16 L1 Δ310 was identified as having the appropriate twenty-seven nucleotide deletion and this construct was used to insert DNA fragments encoding other HPV 16 proteins at the EcoRV site as discussed below.

B. Generation of an HPV 16 L1 ΔC Expression Constructs

Two primers (SEQ ID NOs: 7 and 8) were designed complementary to the HPV 16 L1 open reading frame such that the primers abutted each other to permit amplification in reverse directions on the template DNA comprising HPV 16 L1-encoding sequences in pUC19 described above.

AAA<u>GATATC</u>TTGTAGTAAAAATTTGCGTCCTAAAGGAAAC    SEQ ID NO:7

AAA<u>GATATC</u>TAATCTACCTCTACAACTGCTAAACGCAAAAACG    SEQ ID NO:8

Each primer introduced an EcoRV restriction site at the terminus of the amplification product. In the downstream primer (SEQ ID NO: 8), the EcoRV site was followed by a TAA translational stop codon positioned such that the amplification product, upon ligation of the EcoRV ends to circularize, would include deletion of the 34 carboxy terminal L1 amino acids. PCR was performed to amplify the partial L1 open reading frame and the complete vector. The amplification product was cleaved with EcoRV, circularized with T4 DNA ligase, and transformed into *E. coli* DH5 α cells. Plasmids from viable clones were analyzed for the presence of an EcoRV site which would linearize the plasmid. One positive construct designated pUCHPV16L1ΔC was identified and used to insert DNA from other HPV 16 proteins utilizing the EcoRV site.

C. Insertion of DNA fragments into HPV 16 L1 Δ310 and HPV16L1ΔC

DNA fragments of HPV 16 E7 encoding amino acids 1–50, 1–60, 1–98, 25–75, 40–98, 50–98 in SEQ ID NO: 4 were amplified using primers that introduced terminal 5' EcoRV restriction sites in order to facilitate insertion of the fragment into either HPV 16 L1 Δ310 and HPV16L1ΔC modified sequence. In the various amplification reactions, primer E7.1 (SEQ ID NO: 9) was used in combination with primer E7.2 (SEQ ID NO: 10) to generate a DNA fragment encoding E7 amino acids 1–50: with primer E7.3 (SEQ ID NO: 11) generate a DNA fragment encoding E7 amino acids 1–60: or with primer E7.4 (SEQ ID NO: 12) generate a DNA fragment encoding E7 amino acids 1–98. In other amplification reactions, primer pairs E7.5 (SEQ ID NO: 13) and E7.6 (SEQ ID NO: 14) were used to amplify a DNA fragment encoding E7 amino acids 25–75: E7.7 (SEQ ID NO: 15) and E7.4 (SEQ ID NO: 12) were used to amplify a DNA fragment encoding E7 amino acids 40–98; and E7.8 (SEQ ID NO: 16) and E7.4 (SEQ ID NO: 12) were used to amplify a DNA fragment encoding E7 amino acids 50–98.

was determined utilizing a NsII restriction site within the E7 coding region.

Once expression constructs having appropriate inserts were identified, the protein coding region for both L1 and inserted amino acids was excised as a unit using restriction enzymes XbaI and SmaI and the isolated DNA ligated into plasmid pVL1393 (Invitrogen) to generate recombinant baculoviruses.

D. Elimination of EcoRV Restriction Sites in Expression Constructs

The HPV 16 L1 ΔC sequence includes DNA from the EcoRV site that results in translation of amino acids not normally found in wild-type L1 polypeptides. Thus, a series of expression constructions was designed in which the artificial EcoRv site was eliminated. The L1 sequence for

```
Primer E7.1  AAAAGATATCCATGCATGGAGATACACCTACATTGC          SEQ ID NO:9

Primer E7.2  TTTTGATATCGGCTCTGTCCGGTTCTGCTTGTCC            SEQ ID NO:10

Primer E7.3  TTTTGATATCCTTGCAACAAAAGGTTACAATATTGTAATGGGCC  SEQ ID NO:11

Primer E7.4  AAAAGATATCTGGTTTCTGAGAACAGATGGGGCAC           SEQ ID NO:12

Primer E7.5  TTTTGATATCGATTATGAGCAATTAAATGACAGCTCAG        SEQ ID NO:13

Primer E7.6  TTTTGATATCGTCTACGTGTGTGCTTTGTACGCAC           SEQ ID NO:14

Primer E7.7  TTTATCGATATCGGTCCAGCTGGACAAGCAGAACCGGAC       SEQ ID NO:15

Primer E7.8  TTTTGATATCGATGCCCATTACAATATTGTAACCTTTTG       SEQ ID NO:16
```

Similarly, nucleotides from DNA encoding the influenza matrix protein (SEQ ID NO: 17) was amplified using the primer pair set out in SEQ ID NOs: 19 and 20. Both primers introduced an EcoRV restriction site in the amplification product.

```
TTTTGATATCGATATGGAATGGCTAAAGACAAGACCAATC   SEQ ID NO:19

TTTTGATATCGTTGTTTGGATCCCCATTCCCATTG        SEQ ID NO:20
``` this series of expression constructs was designated HPV 16L1ΔC*.

To generate an expression construct containing the HPV 16L1ΔC* sequence, two PCR reactions were preformed to amplify two overlapping fragments from the pUC-HPV16 L1ΔC encoding E7 amino acids 1–50. The resulting DNA fragments overlapped at the position of the L1/E7 boundary but did not contain the two EcoRV restriction sites. Fragment 1 was generated using primers P1 (SEQ ID NO: 21) and P2 (SEQ ID NO: 22) and fragment 2 using primers P3 (SEQ ID NO: 23) and P4 (SEQ ID NO: 24).

```
Primer P1  GTTATGACATACATACATTCTATG                  SEQ ID NO:21

Primer P2  CCATGCATTCCTGCTTGTAGTAAAAATTTGCGTCC       SEQ ID NO:22

Primer P3  CTACAAGCAGGAATGCATGGAGATACACC             SEQ ID NO:23

Primer P4  CATCTGAAGCTTAGTAATGGGCTCTGTCCGGTTCTG      SEQ ID NO:24
```

PCR products from each amplification reaction were cleaved with EcoRV and inserted into the EcoRV site of either the HPV 16 L1 Δ310 and HPV16L1ΔC sequences previously linearized with the same enzyme. In order to determine the orientation of inserts in plasmids encoding E7 amino acids 25–75 and 50–98 and plasmid including influenza matrix protein, ClaI digestion was employed, taking advantage of a restriction site overlapping the newly created EcoRV restriction site (GATATCGAT) and included in the upstream primer. For the three expression constructs including the initiating methionine of HPV16 E7, insert orientation Following the first two amplification reactions, the two purified products were used as templates in another PCR reaction using primers P1 and P4 only. The resulting amplification product was digested with enzymes EcoNI and HindIII inserted into the HPV 16L1 ΔC expression construct described above following digestion with the same enzymes. The resulting expression construct differed from the original HPV16L1ΔC construct with DNA encoding L1 and E7 amino acids 1–50 by loss of the two internal EcoRV restriction sites. The first EcoRV site was replaced by DNA encoding native L1 alanine and glycine amino acids in this position and the second was replaced by a translational stop signal. In addition, the expression constrict, designated HPV 16 L1ΔC* E7 1–52, contained the first 52 amino acids of HPV 16 E7 as a result of using primer P4 which also encodes E7 amino acids residues histidine at position 51 and tyrosine at position 52. HPV 16 L1ΔC* E7 1–52 was then used to generate additional HPV 16 L1 ΔC expression constructs further including DNA encoding E7 amino acids 1–55 using primer P1 (SEQ ID NO: 21) in combination with primer P5 (SEQ ID NO: 25), E7 amino acids 1–60 with primer pair P1 and P6 (SEQ ID NO: 26), and E7 amino acids 1–65 with primer pair P1 and P7 (SEQ ID NO: 27). The additional amino acid-encoding DNA sequences in the amplification products arose from design of the primers to include additional nucleotides for the desired amino acids.

```
Primer P5  CATCTGAAGCTTAACAATATTGTAATGGGCTCTGTCCG                           SEQ ID NO:25

Primer P6  CATCTGAAGCTTACTTGCAACAAAAGGTTACAATATTGTAATGGGCTCTGTCCG           SEQ ID NO:26

Primer P7  CATCTGAAGCTTAAAGCGTAGAGTCACACTTGCAACAAAAGGTTACAATATTGTAATGGGCTCTGTCCG  SEQ ID NO:27
```

Similarly, HPV 16 L1ΔC* E7 1–70 was venerated using template DNA encoding HPV 16 L1ΔC* E7 1–66 and the primer pair P1 and P8 (SEQ ID NO: 28).

```
Primer P8  CATCTGAAGCTTATTGTACGCACAACCGAAGCGTAGAGTCACACTTG   SEQ ID NO:28
```

Following each PCR reaction, the amplification products were digested with EcoNI and HindIII and inserted into HPV16L1ΔC previously digested with the same enzymes. Sequences of each constructs were determined using an Applied Biosystems Prism 377 sequencing instrument with fluorescent chain terminating dideoxynucleotides [Prober et al., *Science* 238:336–341 (1987)].

EXAMPLE 2

Generation of Recombinant Baculoviruses

*Spodoprera frugiperda* (Sf9) cells were grown in suspension or monolayer cultures at 27° in TNMFH medium (Sigma) supplemented with 10% fetal calf serum and 2 mM glutamine. For HPV 16 L1-based recombinant baculovirus construction, Sf9 cells were transfected with 10 μg of transfer plasmid together with 2 μg of linearized Baculo-Gold DNA (PharMingen, San Diego, Calif.) Recombinant viruses were purified by according to manufacturer's suggested protocol.

To test for expression of HPV 16 L1 protein, $10^5$ Sf9 cells were infected with baculovirus recombinant at a multiplicity of infection (m.o.i) of 5 to 10. After incubation for three to four days at 28° C., media was removed and cells were washed with PBS. The cells were lysed in SDS sample buffer and analyzed by SDS-PAGE and Western blotting using anti-HPV16 L1 and anti-HPV16 E7 antibodies.

In order to determine which of the chimeric L1 protein expression constructs would preferentially produce capsomeres, extracts from transfected cells were subjected to gradient centrifugation. Fractions obtained from the gradient were analyzed for L1 protein content by Western blotting and for VLP formation by electron microscopy. The results are shown in Table 1.

The intact HPV L1 protein, as well as the expression products HPV 16 L1Δ310 and HPV 16 L1ΔC, each were shown to produce capsomeres and virus-like particles in equal proportions. When E7 coding sequences were inserted into the HPV 16 L1Δ310 vector, only fusion proteins including E7 amino acids 1 to 50 produced gave rise to detectable capsomere formation.

When E7 encoding DNA was inserted into the HPV 16 L1ΔC vector, all fusion proteins were found to produce capsomeres; chimeric proteins including E7 amino acid residues 40–98 produced the highest level of exclusively capsomere structures. Chimeric proteins including E7 amino acids 1–98 and 25–75 both produced predominantly capsomeres, even thorough virus-like particle formation was also observed. The chimeric protein including E7 amino acids 1–60 resulted in nearly equal levels of capsomere and virus-like particle production.

When E7 sequences were inserted into the HPV 16 L1Δ*C vector, all fusion proteins were shown to produce capsomeres. Insertion of DNA encoding E7 residues 1–52, 1–55, and 1–60 produced the highest level of capsomeres, but equal levels of virus-like particle production were observed. While insertion of DNA encoding E7 DNA for residues 1–65, 1–70, 25–75, 40–98, and 1–98 resulted in comparatively lower levels or undetectable levels of capsid, capsomeres were produced in high quantities.

TABLE 1

| Capsomeree and Capsid Forming Capacity of Chimeric HPV L1 Proteins | | | |
|---|---|---|---|
| L1 Expression Construct | Insert | Capsomere Yield | Capsid Yield |
| HVP 16 L1 | None | +++++ | +++++ |
| HPV 16 L1Δ310 | None | +++ | ++ |
| HPV 16 L1ΔC | None | ++++ | ++++ |
| HPV 16 L1Δ310 | E7 1–98 | − | − |
| HPV 16 L1Δ310 | E7 1–50 | ++ | − |
| HPV 16 L1Δ310 | E7 25–75 | − | − |
| HPV 16 L1Δ310 | E7 50–98 | − | − |
| HPV 16 L1ΔC | E7 1–98 | +++ | + |
| HPV 16 L1ΔC | E7 25–75 | +++ | + |
| HPV 16 L1ΔC | E7 50–98 | + | + |
| HPV 16 L1ΔC | E7 1–60 | +++++ | +++++ |
| HPV 16 L1ΔC | E7 40–98 | ++++ | − |
| HPV 16 L1ΔC | Influenza | +++ | + |
| HPV 16 L1Δ*C | E7 1–52 | +++++ | +++++ |
| HPV 16 L1Δ*C | E7 1–55 | +++++ | +++++ |
| HPV I6 L1Δ*C | E7 1–60 | +++ | ++++ |
| HPV 16 L1Δ*C | E7 1–65 | ++ | − |
| HPV 16 L1Δ*C | E7 1–70 | ++ | − |

EXAMPLE 3

Purification of Capsomeres

*Trichopulsia ni* (TN) High Five cells were grown to a density of approximately $2 \times 10^6$ cells/ml in Ex-Cell 405 serum-free medium (JRH Biosciences). Approximately $2 \times 10^8$ cells were pelleted by centrifugation at 1000×g for 15 minutes, resuspended in 20 ml of medium, and infected with recombinant baculoviruses at m.o.i of 2 to 5 for 1 hour at room temperature. After addition of 200 ml medium, cells were plated and incubated for 3 to 4 days at 27° C. Following incubation, cells were harvested, pelleted, and resuspended in 10 ml of extraction buffer.

The following steps were performed at 4° C. Cells were sonicated for 45 seconds at 60 watts and the resulting cell lysate was centrifuged at 10,000 rpm in a Sorval SS34 rotor. The supernatant was removed and retained while the resulting pellet was resuspended in 6 ml of extraction buffer, sonicated for an additional 3 seconds at 60 watts, and centrifuged again. The two supernatants were combined, layered onto a two-step gradient containing 14 ml of 40% sucrose on top of 8 ml of CsCl solution (4.6 g CsCl per 8 ml in extraction buffer), and centrifuged in a Sorval AH629 swinging bucket rotor for 2 hours at 27,000 rpm at 10° C. The interface region between the CsCl and the sucrose along with the CsCl complete layer were collected into 13.4 ml Quickseal tubes (Beckman) and extraction buffer added to adjust the volume 13.4 ml. Samples were centrifuged overnight at 50,000 rpm at 20° C. in a Beckman 70 TI rotor. Gradients were fractionated (1 ml per fraction) by puncturing tubes on top and bottom with a 21-gauge needle. Fractions were collected from each tube and 2.5 µl of each fraction were analyzed by a 10% SDS-polyacrylamide gel and Western blotting using an anti-HPV16 L1 antibody.

Virus-like particles and capsomeres were separated from the fractions identified above by sedimentation on 10 to 50% sucrose gradients. Peak fractions from CsCl gradients were pooled and dialyzed for 2 hours against 5 mM HEPES (pH 7.5). Half of the dialysate was used to produce capsomeres by disassembly of intact VLPs overnight by adding EDTA (final concentration 50 mM), EGTA (50 mM), DTT (30 mM), NaCl (100 mM), and Tris/HCl, pH 8.0, (10 mM). As control, NaCl and Tris/HCl only were added to the other half.

For analysis of capsomeres produced from disassembled VLPs, EDTA, EGTA, and DTT (final concentration 5 mM each) were added to the sucrose cushions which were centrifuged at 250,000×g for 2 to 4 hours at 4° C. Fractions were collected by puncturing tubes from the bottom. A 1:10 dilution of each fraction was then analyzed by antigen capture ELISA.

EXAMPLE 4

Immunization Protocol for Production of Polyclonal Antisera and Monoclonal Antibodies Balb/c mice are immunized subcutaneously three times, every four weeks with approximately 60 µg of HPV chimeric capsomeres mixed 1:1 with complete or incomplete Freund's Adjuvants in a total volume of 100 µl. Six weeks after the third immunization, mice are sacrificed and blood is collected by cardiac puncture.

EXAMPLE 5

Peptide ELISA to Quantitate Capsomere Formation

Microtiter plates (Dynatech) are coated overnight with 50 µl of peptide E701 [Muller et al., 1982] at a concentration of 10 µg/ml in PBS. Wells are blocked for 2 hour at 37° C. with 100 µl of buffer containing 5% BSA and 0.05% Tween 20 in PBS and washed three times with PBS containing 0.05% Tween 20. After the third wash, 50 µl of sera diluted 1:5000 in BSA/Tween 20/PBS is added to each well and incubation carried out for 1 hour. Plates are washed again as before and 50 µl of goat-anti-mouse peroxidase conjugate is added at a 1:5000 dilution. After 1 hour, plates are washed and stained using ABTS substrate (0.2 mg/ml, 2,2'-Azino-bis(3-ethylbenzhiazoline-β-sulfonic acid in 0.1 M Na-Acetate-Phosphate buffer (pH 4.2) with 4 µl 30% $H_2O_2$ per 10 ml). Extinction is measured after 1 hour at 490 nm in a Dynatech automated plate reader.

EXAMPLE 6

Antigen Capture ELISA to Quantitate Capsomere Formation

To allow relative quantification of virus-like particles and capsomeres in fractions of CsCl gradients, an antigen capture ELISA was utilized. Microtiter plates were coated overnight with 50 µl/well of a 1:500 dilution (final concentration of 2 µg per ml, in PBS) with a protein A purified mouse monoclonal antibody immunospecific for HPV 16 L1 (antibodies 25/C, MM07 and Ritti 1 were obtained from mice immunized with HPV 16 VLPs). Plates were blocked with 5% milk/PBS for 1 hour and 50 µl of fractions of CsCl gradients were added for 1 hour at 37° C. using a 1:300 dilution (in 5% milk/PBS). After three washings with PBS/ 0.05% Tween 20, 50 µl of a polyclonal rabbit antiserum (1:3000 dilution in milk/PBS), raised against HPV 16 VLPs was added and plates were incubated at 375 for 1 hour. Plates were washed again and further incubated with 50 µl of a goat-anti-rabbit peroxidase conjugate (Sigma) diluted 1:5000 in PBS containing 5% milk for 1 hour. After final washing, plates were stained with ABTS substrate for 30 minutes and extinction measured at 490 nm in a Dynatech automated plate reader. As a negative control, the assay also included wells coated only with PBS.

To test monoclonal antibodies for capsomere specificity, VLPs with EDTA/DTT to disassemble particles. Treated particle preparations were assayed in the antigen-capture ELISA and readings compared to untreated controls. For disassembly, 40 µl of VLPs was incubated overnight at 4° C. in 500 µl of disruption buffer containing 30 mM DTT. 50 mM EGTA, 60 mM EDTA, 100 mM NaCl, and 100 mM Tris/HCl, pH 8.0. Aliquots of treated and untreated particles were used in the above capture ELISA in a 1:20–1:40 dilution.

EXAMPLE 7

Hemagglutinin Inhibition Assay

In order to determine the extent to which chimeric capsomere vaccines evoke production of neutralizing antibodies, a hemagglutination inhibition assay is carried out as briefly described below. This assay is based on previous observations that virus-like particles are capable of hemagglutinizing red blood cells.

Mice are immunized with any of a chimeric capsomere vaccine and sera is collected as described above in Example 4. As positive controls, BPV16 L1 virus like particles (VLPs) and bovine PV1 (BPV) L1 VLPs are assayed in parallel with a chimeric capsomere preparation. To establish a positive baseline, the HPV 16 or BPV1 VLPs are first incubated with or without sera collected from immunized mice after which red blood cells are added. The extent to which preincubation with mouse cera inhibits red blood cell hemagglutinization is an indication of the neutralizing capacity of the mouse sera. The experiments are then repeated using chimeric capsomeres in order to determine the neutralizing effect of the mouse sera on the vaccine. A brief protocol for the hemagglutination inhibition assay is described below.

One hundred microliters of heparin (1000 usp units/ml) are added to 1 ml fresh mouse blood. Red blood cells are washed three times with PBS followed by centrifugation and resuspension in a volume of 10 ml. Next, erythrocytes are resuspended in 0.5 ml PBS and stored at 4° C. for up to three days. For the hemagglutinin assay. 70 μl of the suspension is used per well on a 96-well plate.

Chimeric capsomere aliquots from CsCl gradients are dialyzed for one hour against 10 mM Hepes (pH 7.5) and 100 μl of two-fold serial dilutions in PBS are added to mouse erythrocytes in round-bottom 96-well microtiter plates which are further incubated for 3–16 hours at 4° C. For hemagglutination inhibition, capsomeres are incubated with dilutions of antibodies in PBS for 60 minutes at room temperature and then added to the erythrocytes. The level of erythrocyte hemagglutination, and therefore the presence of neutralizing antibodies, is determined by standard methods.

In preliminary results, mouse sera generated against chimeric capsomeres comprising HPV16L1ΔC protein in association with E7 amino acid residues 1–98 was observed to inhibit hemagglutination by HPV16 VLPs, but not by BPV VLPs. The mouse sera was therefore positive for neutralizing antibodies against the human VLPs and this differential neutralization was most likely the result of antibody specificity for epitopes against which the antibodies were raised.

Numerous modifications and variations in the invention as set forth in the above illustrative examples are expected to occur to those skilled in the art Consequently only such limitations as appear in the appended claims should be placed on the invention.

What is claimed is:

1. A protein encoded by a nucleic acid molecule which is HPV 16L1ΔC* encoding a truncated HPV L1 protein.

2. A protein encoded by a nucleic acid molecule encoding a fusion protein, said fusion protein comprising an HPV E7 protein and a truncated HPV L1 protein, said truncated HPV L1 protein consisting of an amino acid sequence encoded by HPV 16L1ΔC*.

3. A protein of claim 1 wherein said HPV E7 protein comprises amino acids 1–52 of an HPV E7 protein.

4. A protein of claim 2 wherein said HPV E7 protein comprises amino acids 1–52 of SEQ ID NO: 4.

5. A protein of claim 1 wherein said HPV E7 protein comprises amino acids 1–55 of an HPV E7 protein.

6. A protein of claim 5 wherein said HPV E7 protein comprises amino acids 1–55 of SEQ ID NO: 4.

7. A protein of claim 1 wherein said HPV E7 protein comprises amino acids 1–60 of an HPV E7 protein.

8. A protein of claim 7 wherein said HPV E7 protein comprises amino acids 1–60 of SEQ ID NO: 4.

9. A protein of claim 1 wherein said HPV E7 protein comprises amino acids 1–65 of an HPV E7 protein.

10. A protein of claim 9 wherein said HPV E7 protein comprises amino acids 1–65 of SEQ ID NO: 4.

11. A protein of claim 1 wherein said HPV E7 protein comprises amino acids 1–70 of an HPV E7 protein.

12. A protein of claim 11 wherein said HPV E7 protein comprises amino acids 1–70 of SEQ ID NO: 4.

13. A method of treating a patient infected with HPV comprising administering a pharmaceutical composition comprising the protein of claim 1 in an amount effective to reduce the level of HPV infection.

14. A method of treating a patient infected with HPV comprising administering a pharmaceutical composition comprising the protein of claim 2 in an amount effective to reduce the level of HPV infection.

15. A method of preventing HPV infection comprising administering a pharmaceutical composition comprising the protein of claim 1 in an amount effective to prevent HPV infection.

16. A method of preventing HPV infection comprising administering a pharmaceutical composition comprising the protein of claim 2 in an amount effective to prevent HPV infection.

* * * * *

UNITED STATES PATENT AND TRADEMARK OFFICE
CERTIFICATE OF CORRECTION

PATENT NO.    : 6,562,351 B2
DATED         : May 13, 2003
INVENTOR(S)   : Alexander Burger and Michael Hallek It is certified that error appears in the above-identified patent and that said Letters Patent is hereby corrected as shown below:

Title page,
Item [54], Title, please change the Title to read -- PAPILLOMA VIRUS TRUNCATED L1 PROTEIN AND FUSION PROTEIN CONTRUCTS --.
Item [75], Inventors, please change the first named inventor to -- Alexander Burger --.

Signed and Sealed this

Twenty-third Day of September, 2003

JAMES E. ROGAN
*Director of the United States Patent and Trademark Office*

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1515

(xi) SEQUENCE DESCRIPTION: SEQ ID NO: 1:

```
ATG TCT CTT TGG CTG CCT AGT GAG GCC ACT GTC TAC TTG CCT CCT GTC         48
Met Ser Leu Trp Leu Pro Ser Glu Ala Thr Val Tyr Leu Pro Pro Val
 1               5                  10                  15

CCA GTA TCT AAG GTT GTA AGC ACG GAT GAA TAT GTT GCA CGC ACA AAC         96
Pro Val Ser Lys Val Val Ser Thr Asp Glu Tyr Val Ala Arg Thr Asn
                20                  25                  30

ATA TAT TAT CAT GCA GGA ACA TCC AGA CTA CTT GCA GTT GGA CAT CCC        144
Ile Tyr Tyr His Ala Gly Thr Ser Arg Leu Leu Ala Val Gly His Pro
            35                  40                  45

TAT TTT CCT ATT AAA AAA CCT AAC AAT AAC AAA ATA TTA GTT CCT AAA        192
Tyr Phe Pro Ile Lys Lys Pro Asn Asn Asn Lys Ile Leu Val Pro Lys
    50                  55                  60

GTA TCA GGA TTA CAA TAC AGG GTA TTT AGA ATA CAT TTA CCT GAC CCC        240
Val Ser Gly Leu Gln Tyr Arg Val Phe Arg Ile His Leu Pro Asp Pro
65                  70                  75                  80

AAT AAG TTT GGT TTT CCT GAC ACC TCA TTT TAT AAT CCA GAT ACA CAG        288
Asn Lys Phe Gly Phe Pro Asp Thr Ser Phe Tyr Asn Pro Asp Thr Gln
                85                  90                  95

CGG CTG GTT TGG GCC TGT GTA GGT GTT GAG GTA GGT CGT GGT CAG CCA        336
Arg Leu Val Trp Ala Cys Val Gly Val Glu Val Gly Arg Gly Gln Pro
                100                 105                 110

TTA GGT GTG GGC ATT AGT GGC CAT CCT TTA TTA AAT AAA TTG GAT GAC        384
Leu Gly Val Gly Ile Ser Gly His Pro Leu Leu Asn Lys Leu Asp Asp
            115                 120                 125

ACA GAA AAT GCT AGT GCT TAT GCA GCA AAT GCA GGT GTG GAT AAT AGA        432
```

```
Thr Glu Asn Ala Ser Ala Tyr Ala Ala Asn Ala Gly Val Asp Asn Arg
    130                 135                 140

GAA TGT ATA TCT ATG GAT TAC AAA CAA ACA CAA TTG TGT TTA ATT GGT           480
Glu Cys Ile Ser Met Asp Tyr Lys Gln Thr Gln Leu Cys Leu Ile Gly
145                 150                 155                 160

TGC AAA CCA CCT ATA GGG GAA CAC TGG GGC AAA GGA TCC CCA TGT ACC           528
Cys Lys Pro Pro Ile Gly Glu His Trp Gly Lys Gly Ser Pro Cys Thr
                165                 170                 175

AAT GTT GCA GTA AAT CCA GGT GAT TGT CCA CCA TTA GAG TTA ATA AAC           576
Asn Val Ala Val Asn Pro Gly Asp Cys Pro Pro Leu Glu Leu Ile Asn
            180                 185                 190

ACA GTT ATT CAG GAT GGT GAT ATG GTT GAT ACT GGC TTT GGT GCT ATG           624
Thr Val Ile Gln Asp Gly Asp Met Val Asp Thr Gly Phe Gly Ala Met
        195                 200                 205

GAC TTT ACT ACA TTA CAG GCT AAC AAA AGT GAA GTT CCA CTG GAT ATT           672
Asp Phe Thr Thr Leu Gln Ala Asn Lys Ser Glu Val Pro Leu Asp Ile
    210                 215                 220

TGT ACA TCT ATT TGC AAA TAT CCA GAT TAT ATT AAA ATG GTG TCA GAA           720
Cys Thr Ser Ile Cys Lys Tyr Pro Asp Tyr Ile Lys Met Val Ser Glu
225                 230                 235                 240

CCA TAT GGC GAC AGC TTA TTT TTT TAT TTA CGA AGG GAA CAA ATG TTT           768
Pro Tyr Gly Asp Ser Leu Phe Phe Tyr Leu Arg Arg Glu Gln Met Phe
                245                 250                 255

GTT AGA CAT TTA TTT AAT AGG GCT GGT GCT GTT GGT GAA AAT GTA CCA           816
Val Arg His Leu Phe Asn Arg Ala Gly Ala Val Gly Glu Asn Val Pro
            260                 265                 270

GAC GAT TTA TAC ATT AAA GGC TCT GGG TCT ACT GCA AAT TTA GCC AGT           864
Asp Asp Leu Tyr Ile Lys Gly Ser Gly Ser Thr Ala Asn Leu Ala Ser
        275                 280                 285

TCA AAT TAT TTT CCT ACA CCT AGT GGT TCT ATG GTT ACC TCT GAT GCC           912
Ser Asn Tyr Phe Pro Thr Pro Ser Gly Ser Met Val Thr Ser Asp Ala
    290                 295                 300

CAA ATA TTC AAT AAA CCT TAT TGG TTA CAA CGA GCA CAG GGC CAC AAT           960
Gln Ile Phe Asn Lys Pro Tyr Trp Leu Gln Arg Ala Gln Gly His Asn
305                 310                 315                 320

AAT GGC ATT TGT TGG GGT AAC CAA CTA TTT GTT ACT GTT GTT GAT ACT          1008
Asn Gly Ile Cys Trp Gly Asn Gln Leu Phe Val Thr Val Val Asp Thr
                325                 330                 335

ACA CGC AGT ACA AAT ATG TCA TTA TGT GCT GCC ATA TCT ACT TCA GAA          1056
Thr Arg Ser Thr Asn Met Ser Leu Cys Ala Ala Ile Ser Thr Ser Glu
            340                 345                 350

ACT ACA TAT AAA AAT ACT AAC TTT AAG GAG TAC CTA CGA CAT GGG GAG          1104
Thr Thr Tyr Lys Asn Thr Asn Phe Lys Glu Tyr Leu Arg His Gly Glu
        355                 360                 365

GAA TAT GAT TTA CAG TTT ATT TTT CAA CTG TGC AAA ATA ACC TTA ACT          1152
Glu Tyr Asp Leu Gln Phe Ile Phe Gln Leu Cys Lys Ile Thr Leu Thr
    370                 375                 380

GCA GAC GTT ATG ACA TAC ATA CAT TCT ATG AAT TCC ACT ATT TTG GAG          1200
Ala Asp Val Met Thr Tyr Ile His Ser Met Asn Ser Thr Ile Leu Glu
385                 390                 395                 400

GAC TGG AAT TTT GGT CTA CAA CCT CCC CCA GGA GGC ACA CTA GAA GAT          1248
Asp Trp Asn Phe Gly Leu Gln Pro Pro Pro Gly Gly Thr Leu Glu Asp
                405                 410                 415

ACT TAT AGG TTT GTA ACC TCC CAG GCA ATT GCT TGT CAA AAA CAT ACA          1296
Thr Tyr Arg Phe Val Thr Ser Gln Ala Ile Ala Cys Gln Lys His Thr
            420                 425                 430

CCT CCA GCA CCT AAA GAA GAT CCC CTT AAA AAA TAC ACT TTT TGG GAA          1344
Pro Pro Ala Pro Lys Glu Asp Pro Leu Lys Lys Tyr Thr Phe Trp Glu
        435                 440                 445
```

```
GTA AAT TTA AAG GAA AAG TTT TCT GCA GAC CTA GAT CAG TTT CCT TTA      1392
Val Asn Leu Lys Glu Lys Phe Ser Ala Asp Leu Asp Gln Phe Pro Leu
    450                 455                 460

GGA CGC AAA TTT TTA CTA CAA GCA GGA TTG AAG GCC AAA CCA AAA TTT      1440
Gly Arg Lys Phe Leu Leu Gln Ala Gly Leu Lys Ala Lys Pro Lys Phe
465                 470                 475                 480

ACA TTA GGA AAA CGA AAA GCT ACA CCC ACC ACC TCA TCT ACC TCT ACA      1488
Thr Leu Gly Lys Arg Lys Ala Thr Pro Thr Thr Ser Ser Thr Ser Thr
                485                 490                 495

ACT GCT AAA CGC AAA AAA CGT AAG CTG TAA                              1518
Thr Ala Lys Arg Lys Lys Arg Lys Leu
        500                 505
```

(2) INFORMATION FOR SEQ ID NO: 2:

(i) SEQUENCE CHARACTERISTICS:
        (A) LENGTH: 505 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
        210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270
```

```
Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
        290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
        340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
        370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
                500                 505

(2) INFORMATION FOR SEQ ID NO: 3:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..294

(xi) SEQUENCE DESCRIPTION: SEQ ID NO: 3:

ATG CAT GGA GAT ACA CCT ACA TTG CAT GAA TAT ATG TTA GAT TTG CAA        48
Met His Gly Asp Thr Pro Thr Leu His Glu Tyr Met Leu Asp Leu Gln
  1               5                  10                  15

CCA GAG ACA ACT GAT CTC TAC TGT TAT GAG CAA TTA AAT GAC AGC TCA        96
Pro Glu Thr Thr Asp Leu Tyr Cys Tyr Glu Gln Leu Asn Asp Ser Ser
                 20                  25                  30

GAG GAG GAG GAT GAA ATA GAT GGT CCA GCT GGA CAA GCA GAA CCG GAC       144
Glu Glu Glu Asp Glu Ile Asp Gly Pro Ala Gly Gln Ala Glu Pro Asp
             35                  40                  45

AGA GCC CAT TAC AAT ATT GTA ACC TTT TGT TGC AAG TGT GAC TCT ACG       192
Arg Ala His Tyr Asn Ile Val Thr Phe Cys Cys Lys Cys Asp Ser Thr
         50                  55                  60

CTT CGG TTG TGC GTA CAA AGC ACA CAC GTA GAC ATT CGT ACT TTG GAA       240
```

```
Leu Arg Leu Cys Val Gln Ser Thr His Val Asp Ile Arg Thr Leu Glu
 65                  70                  75                  80

GAC CTG TTA ATG GGC ACA CTA GGA ATT GTG TGC CCC ATC TGT TCT CAG       288
Asp Leu Leu Met Gly Thr Leu Gly Ile Val Cys Pro Ile Cys Ser Gln
                 85                  90                  95

AAA CCA TAA                                                           297
Lys Pro
```

(2) INFORMATION FOR SEQ ID NO: 4:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO: 4:

```
Met His Gly Asp Thr Pro Thr Leu His Glu Tyr Met Leu Asp Leu Gln
 1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
                 35                  40                  45

Arg Ala His Tyr Asn Ile Val Thr Phe Cys Cys Lys Cys Asp Ser Thr
         50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro
```

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 5:

CCCCGATATC GCCTTTAATG TATAAATCGT CTGG                                 34

(2) INFORMATION FOR SEQ ID NO: 6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 6:

CCCCGATATC TCAAATTATT TTCCTACACC TAGTG                                35

(2) INFORMATION FOR SEQ ID NO: 7:

(i) SEQUENCE CHARACTERISTICS:
        (A) LENGTH: 40 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 7:

AAAGATATCT TGTAGTAAAA ATTTGCGTCC TAAAGGAAAC                          40

(2) INFORMATION FOR SEQ ID NO: 8:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 8:

AAAGATATCT AATCTACCTC TACAACTGCT AAACGCAAAA AACG                     44

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 9:

AAAAGATATC ATGCATGGAG ATACACCTAC ATTGC                               35

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 10:

TTTTGATATC GGCTCTGTCC GGTTCTGCTT GTCC                                34

(2) INFORMATION FOR SEQ ID NO: 11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 11:

TTTTGATATC CTTGCAACAA AAGGTTACAA TATTGTAATG GGCC                     44

(2) INFORMATION FOR SEQ ID NO: 12:

(i) SEQUENCE CHARACTERISTICS:

(A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 12:

AAAAGATATC TGGTTTCTGA GAACAGATGG GGCAC                                    35

(2) INFORMATION FOR SEQ ID NO: 13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 13:

TTTTGATATC GATTATGAGC AATTAAATGA CAGCTCAG                                 38

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 14:

TTTTGATATC GTCTACGTGT GTGCTTTGTA CGCAC                                    35

(2) INFORMATION FOR SEQ ID NO: 15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 15:

TTTATCGATA TCGGTCCAGC TGGACAAGCA GAACCGGAC                                39

(2) INFORMATION FOR SEQ ID NO: 16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 16:

TTTTGATATC GATGCCCATT ACAATATTGT AACCTTTTG                                39

(2) INFORMATION FOR SEQ ID NO: 17:

(i) SEQUENCE CHARACTERISTICS:
    (A) LENGTH: 294 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..291

(xi) SEQUENCE DESCRIPTION: SEQ ID NO: 17:

```
ATG AGT CTT CTA ACC GAG GTC GAA ACG CTT ACC AGA AAC GGA TGG GAG      48
Met Ser Leu Leu Thr Glu Val Glu Thr Leu Thr Arg Asn Gly Trp Glu
 1               5                  10                  15

TGC AAA TGC AGC GAT TCA AGT GAT CCT CTC ATT ATC GCA GCG AGT ATC      96
Cys Lys Cys Ser Asp Ser Ser Asp Pro Leu Ile Ile Ala Ala Ser Ile
                20                  25                  30

ATT GGG ATC TTG CAC TTG ATA TTG TGG ATT TTT TAT CGT CTT TTC TTC     144
Ile Gly Ile Leu His Leu Ile Leu Trp Ile Phe Tyr Arg Leu Phe Phe
            35                  40                  45

AAA TGC ATT TAT CGT CGC CTT AAA TAC GGT TTG AAA AGA GGG CCT TCT     192
Lys Cys Ile Tyr Arg Arg Leu Lys Tyr Gly Leu Lys Arg Gly Pro Ser
 50                  55                  60

ACG GAA GGA GCG CCT GAG TCT ATG AGG GAA GAA TAT CGG CAG GAA CAG     240
Thr Glu Gly Ala Pro Glu Ser Met Arg Glu Glu Tyr Arg Gln Glu Gln
 65              70                  75                  80

CAG AGT GCT GTG GAT GTT GAC GAT GTT CAT TTT GTC AAC ATA GAG CTG     288
Gln Ser Ala Val Asp Val Asp Asp Val His Phe Val Asn Ile Glu Leu
                85                  90                  95

GAG TAA                                                              294
Glu
```

(2) INFORMATION FOR SEQ ID NO: 18:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Ser Leu Leu Thr Glu Val Glu Thr Leu Thr Arg Asn Gly Trp Glu
 1               5                  10                  15

Cys Lys Cys Ser Asp Ser Ser Asp Pro Leu Ile Ile Ala Ala Ser Ile
                20                  25                  30

Ile Gly Ile Leu His Leu Ile Leu Trp Ile Phe Tyr Arg Leu Phe Phe
            35                  40                  45

Lys Cys Ile Tyr Arg Arg Leu Lys Tyr Gly Leu Lys Arg Gly Pro Ser
 50                  55                  60

Thr Glu Gly Ala Pro Glu Ser Met Arg Glu Glu Tyr Arg Gln Glu Gln
 65              70                  75                  80

Gln Ser Ala Val Asp Val Asp Asp Val His Phe Val Asn Ile Glu Leu
                85                  90                  95

Glu
```

(2) INFORMATION FOR SEQ ID NO: 19:

(i) SEQUENCE CHARACTERISTICS:
        (A) LENGTH: 40 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 19:

TTTTGATATC GATATGGAAT GGCTAAAGAC AAGACCAATC                                40

(2) INFORMATION FOR SEQ ID NO: 20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 20:

TTTTGATATC GTTGTTTGGA TCCCCATTCC CATTG                                     35

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 21:

GTTATGACAT ACATACATTC TATG                                                 24

(2) INFORMATION FOR SEQ ID NO: 22:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 22:

CCATGCATTC CTGCTTGTAG TAAAAATTTG CGTCC                                     35

(2) INFORMATION FOR SEQ ID NO: 23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 23:

CTACAAGCAG GAATGCATGG AGATACACC                                            29

(2) INFORMATION FOR SEQ ID NO: 24:

(i) SEQUENCE CHARACTERISTICS:
        (A) LENGTH: 36 base pairs
```

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 24:

CATCTGAAGC TTAGTAATGG GCTCTGTCCG GTTCTG                              36

(2) INFORMATION FOR SEQ ID NO: 25:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 25:

CATCTGAAGC TTATCAATAT TGTAATGGGC TCTGTCCG                            38

(2) INFORMATION FOR SEQ ID NO: 26:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 26:

CATCTGAAGC TTACTTGCAA CAAAAGGTTA CAATATTGTA ATGGGCTCTG TCCG          54

(2) INFORMATION FOR SEQ ID NO: 27:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 27:

CATCTGAAGC TTAAAGCGTA GAGTCACACT TGCAACAAAA GGTTACAATA TTGTAATGGG    60

CTCTGTCCG                                                           69

(2) INFORMATION FOR SEQ ID NO: 28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 28:

CATCTGAAGC TTATTGTACG CACAACCGAA GCGTAGAGTC ACACTTG                  47
```